United States Patent [19]

Epstein et al.

[11] Patent Number: 4,544,665
[45] Date of Patent: * Oct. 1, 1985

[54] 1-ARYL-3-AZABICYCLO[3.2.0]HEPTANES

[75] Inventors: Joseph W. Epstein, Monroe, N.Y.; Thomas C. McKenzie, Tuscaloosa, Ala.; William J. Fanshawe, Pearl River, N.Y.

[73] Assignee: American Cyanamid Company, Stamford, Conn.

[*] Notice: The portion of the term of this patent subsequent to Feb. 14, 2001 has been disclaimed.

[21] Appl. No.: 553,676

[22] Filed: Nov. 21, 1983

[51] Int. Cl.$^4$ .................... C07D 209/52; A61K 31/40
[52] U.S. Cl. .................................... 514/412; 548/515
[58] Field of Search .......................... 548/515; 514/412

[56] References Cited

U.S. PATENT DOCUMENTS 4,431,661  2/1984  McKenzie et al. ................ 548/411

Primary Examiner—Donald G. Daus
Assistant Examiner—William A. Teoli, Jr.
Attorney, Agent, or Firm—M.-E. M. Timbers

[57] ABSTRACT

This invention concerns 1-aryl-3-azabicyclo[3.2.0]heptanes and their acid-addition salts. More particularly, this invention pertains to compositions useful for treatment of depression in warm-blooded animals.

16 Claims, No Drawings

1-ARYL-3-AZABICYCLO[3.2.0]HEPTANES

DESCRIPTION OF THE INVENTION

The 1-aryl-3-azabicyclo[3.2.0]heptanes of the present invention may be represented by Formula I:

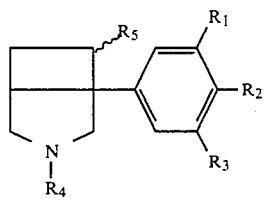

FORMULA I wherein $R_1$, $R_2$ and $R_3$ are each individually selected from the group consisting of hydrogen, hydroxyl, chloro, fluoro, bromo, an alkyl radical having up to 3 carbon atoms, an alkoxyl radical having up to 3 carbon atoms, and trifluoromethyl, and any two or more of $R_1$, $R_2$ and $R_3$ may be the same; $R_4$ is selected from the group consisting of hydrogen and an alkyl radical having up to 3 carbon atoms; and $R_5$ can be either hydrogen, or an alkoxyl radical. The 1-aryl-3-azabicyclo[3.2.0]heptanes of the instant invention include, as well, all non-toxic, pharmacologically acceptable, acid-addition salts thereof.

The various subscripts and symbols for chemical moieties, once defined herein, continue to have the same definition unless otherwise expressly stated.

The compounds of the present invention possess at least two asymmetric carbon atoms and thus can be produced as racemic mixtures or as individual optically active isomers. The racemic mixtures can be resolved if desired at appropriate stages, by methods known to those skilled in the art, to obtain the respective individual isomers.

The free bases of the compounds of this invention are, in general, soluble in organic solvents such as methanol, ethanol, isopropyl alcohol, N,N-dimethylformamide, dimethyl sulfoxide, and the like. They form acid-addition salts with a variety of organic and inorganic salt-forming reagents. Thus, acid-addition salts, formed by admixture of the organic free base with an equivalent amount of an acid, suitably in a neutral solvent, are formed with such acids as hydrochloric, hydrobromic, phosphoric, sulfuric, citric, fumaric, acetic, ascorbic, and gluconic acid, and the like. These salts are generally soluble in water and in lower alkanols, such as methanol. For anti-depressant purposes, the organic free bases are equivalent to their non-toxic acid-addition salts.

Specific 1-aryl-3-azabicyclo[3.2.0]heptanes of the present invention include:

1-(m-methoxyphenyl)-3-methyl-3-azabicyclo[3.2.0]heptane
1(p-methylphenyl)-3-methyl-3-azabicyclo[3.2.0]heptane, fumarate
1-(p-methylphenyl)-3-methyl-3-azabicyclo[3.2.0]heptane
1-(p-methylphenyl)-3-methyl-3-azabicyclo[3.2.0]heptane, fumarate salt
1-(p-chlorophenyl)-3-methyl-3-azabicyclo[3.2.0]heptane
3-methyl-1-(3',4',5'-trimethoxyphenyl)-3-azabicyclo[3.2.0]heptane
3-methyl-1-phenyl-3-azabicyclo[3.2.0]heptane
1-(m-methoxyphenyl)-3-azabicyclo[3.2.0]heptane
1-(m-methoxyphenyl)-3-propyl-3-azabicyclo[3.2.0]heptane, hydrochloride
1-(3',4'-dichlorophenyl)-3-methyl-3-azabicyclo[3.2.0]heptane
7β-ethoxy-1β-(m-methoxyphenyl)-3-methyl-3-azabicyclo[3.2.0]heptane
7α-ethoxy-1β-(m-methoxyphenyl)-3-methyl-3-azabicyclo[3.2.0]heptane.

The compounds of this invention are useful as anti-depressant agents in warm-blooded animals. The antidepressant properties of these compounds were tested by measuring their ability to counteract depression induced in such animals by the administration of tetrabenazine methanesulfonate. Each test compound was administered intraperitoneally to 10 mice at a dose of about 25 mg/kg of body weight. Approximately thirty minutes later, tetrabenazine methanesulfonate was administered intraperitoneally to each mouse at a dose of about 39 mg/kg of body weight, which dose is known to depress markedly the exploratory behavior of normal mice. Approximately thirty minutes later, the mice were tested for their exploratory behavior as described by E. Greenblatt and A. C. Osterberg, Toxicology and Applied Pharmacology, 7: 556–578 (1965). A compound is considered active if 3 or more of the 10 mice are protected against the tetrabenazine-induced effects.

The results of the test on representative compounds of this invention appear in Table I.

TABLE I

| Tetrabenazine-Induced Depression | |
|---|---|
| Compound | Result |
| 1-(p-methylphenyl)-3-methyl-3-azabicyclo-[3·2·0]heptane, fumarate salt | Active (5/10) |
| 7β-ethoxy-1β-(m-methoxyphenyl)-3-methyl-3-azabicyclo[3·2·0]heptane | Active (3/10) |

The anti-depressant activity of the compounds of this invention was also demonstrated in the following test. Inhibition of tetrabenazine-induced ptosis is observed concomitantly with the inhibition of tetrabenazine-induced depression. Ptosis is defined as more than about 75% closure of palpebral aperture induced in animals by the administration of tetrabenazine methanesulfonate. The compounds were administered intraperitoneally at a dosage of about 25 mg per kilogram of body weight to groups of 10 mice. About thirty minutes later, tetrabenazine methanesulfonate was administered intraperitoneally to each mouse at a dose of about 39 mg/kg. About thirty minutes after the injection of tetrabenazine, the mice were placed on an observation disc and examined for approximately 10 seconds for inhibition of ptosis. Mice exhibiting about 75% or greater opening of palpebral aperture are considered responders. A compound is considered active if 5 or more of 10 mice respond. The results of this test on representative compounds of this invention appear in Table II.

TABLE II

| Tetrabenazine-Induced Ptosis | |
|---|---|
| Compound | Result |
| 1-(p-methylphenyl)-3-methyl-3-azabicyclo-[3·2·0]heptane, fumarate salt | Active (10/10) |
| 7β-ethoxy-1β-(m-methoxyphenyl)-3-methyl-3-azabicyclo[3·2·0]heptane | Active (9/10) |

The activity of the compounds of this invention as anti-depressant agents was also shown in the following test which measures the ability of a test compound to inhibit [³H]-imipramine binding to human platelet membranes. Human platelet concentrates were diluted about 1:20 with antiprotease containing buffer of the following composition:
Approximately 0.12M: sodium chloride
Approximately 0.05M: tris buffer
Approximately 0.005N: potassium chloride
Approximately 0.025: μg/ml aprotinin
Approximately 0.5: μg/ml pepstatin
Approximately $2 \times 10^{-5}$N: bacitracin
Approximately 3 mN: ethylenediaminetetraacetic acid
Approximately 1 mN: ethyleneglycol-bis-(β-aminoethyl ether)-N,N'-tetracetic acid Such buffer was kept at about pH 6.8 to prevent platelet release and aggregation. The diluted platelets were centrifuged at about 2,500 g and then resuspended in about 50 volumes of the same buffer. The cells were then ruptured with a Branson sonicator while the suspension was maintained in an ice bath. The ruptured cells were then centrifuged at about 18,000 g, resuspended in fresh buffer and recentrifuged at about 18,000 g. The resulting membranes were then diluted with the above antiprotease buffer, which had been adjusted to about pH 7.4, and to a protein concentration of about 3.0 mg/ml.

The test compounds were dissolved in dimethylsulfoxide at a concentration of about 50 mM and then diluted about 1:10 in either water, about 0.1M hydrochloric acid or about 0.1M sodium hydroxide. They were then diluted about 1:100 in buffer to about 50 μM, and about 50 μl of this stock solution was placed in triplicate test tubes. The tubes were cooled to about 0° C. and about 200 μl of the following mixture were added:
About 100 μl of 3 mg/ml membrane in buffer
About 50 μl of 15 nM[³H]imipramine in buffer
About 50 μl buffer The tubes were incubated for about 60 minutes at about 0° C. Controls contain either buffer alone (100%) or about 10 μM final of desmethylimipramine (DMI). The samples were diluted with about 5 ml of buffer [0.12M-sodium chloride, 0.05M-tris buffer, 0.005M-potassium chloride (pH 7.4)], vacuum filtered and washed twice with about 5 ml of buffer. Radioactivity was measured in a liquid scintillation counter and the degree of binding was calculated.

A compound is considered active if greater than about 50% inhibition is achieved at a concentration of about 10 μM. The results of this test on representative compounds of this invention appear in Table III.

TABLE III

| Platelet Imipramine Binding | | |
|---|---|---|
| Compound | Result | 10 μM |
| 1-(m-methoxyphenyl)-3-methyl-3-azabicyclo[3 · 2 · 0]heptane, fumarate salt, monohydrate | Active | 99.8% |
| 7β-ethoxy-1β-(m-methoxyphenyl)-3-methyl-3-azabicyclo[3 · 2 · 0]heptane | Active | 94% |
| 7α-ethoxy-1β-(m-methoxyphenyl)-3-methyl-3-azabicyclo[3 · 2 · 0]heptane, fumarate salt | Active | 92% |

Compounds of Formula I, wherein $R_5$ is H, may be prepared by the reduction of a thioketal represented by Formula II:

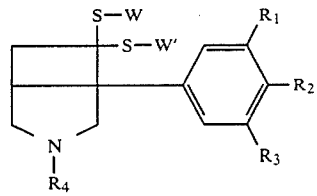

FORMULA II wherein W and W' each represent a monovalent alkyl moiety having up to 3 carbon atoms or W-W' jointly represent a divalent moiety of the formula:

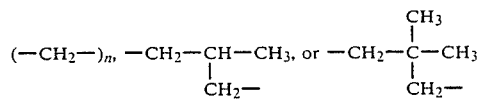

wherein n is the integer 2 or 3, with a catalyst such as Raney nickel in a suitable solvent such as an alcohol, e.g., ethanol or methanol.

Compounds represented by Formula II may be prepared as follows. A ketone, as represented by Formula III

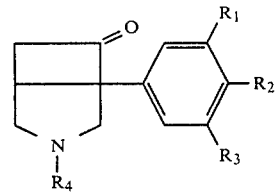

FORMULA III is reacted with a thiol of up to 3 carbon atoms, or a dithiol such as:

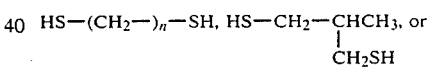

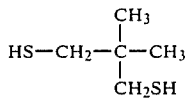

wherein n is the integer 2 or 3, in the presence of a Lewis acid, such as boron trifluoride, in a suitable solvent, such as acetic acid. Ketones as represented by Formula III may be prepared by the hydrolysis of 5-aryl-3-azabicyclo[3.2.0]heptan-6-one ketals with an acid, such as hydrochloric acid. Ketones as represented by Formula III may also be prepared by the reduction of a dichloroketone as represented by Formula IV:

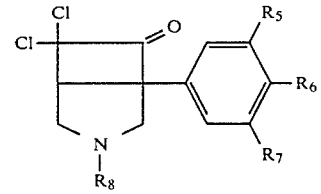

FORMULA IV wherein $R_5$, $R_6$ and $R_7$ are defined the same as $R_1$, $R_2$ and $R_3$, respectively, except $R_5$, $R_6$ and $R_7$ may not be hydroxy, and wherein $R_8$ is the same as $R_4$, except $R_8$ is not hydrogen. The reduction is achieved by reaction of the dichloroketone represented by Formula IV with zinc and acetic acid. A related process is described by P. Crabbe et al., Bull. Soc. Chim. Belg., 86: 109 (1977). The dichloroketones represented by Formula IV may be prepared by interaction of pyrrolines represented by Formula V:

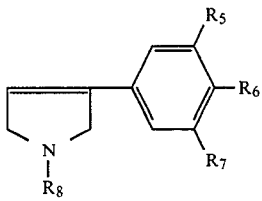

FORMULA V wherein $R_5$, $R_6$, $R_7$ and $R_8$ are as hereinbefore described, with dichloroketone in an aprotic solvent, such as hexane, ether, or tetrahydrofuran. A related process is described by L. Krepski et al., J. Org. Chem., 43: 2879 (1978).

Compounds represented by Formula I, wherein $R_1$, $R_2$ and $R_3$ are each individually selected from the group consisting of hydrogen, hydroxyl, chloro, fluoro, bromo and an alkyl radical having up to 3 carbon atoms, an alkoxyl radical having up to 3 carbon atoms, and trifluoromethyl, and any two or more of $R_1$, $R_2$ and $R_3$ may be the same; $R_4$ is selected from the group consisting of hydrogen and an alkyl radical having up to 3 carbon atoms; and $R_5'$ is an alkoxy radical; may be prepared by the reduction of compounds represented by Formula VI:

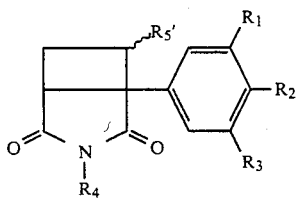

FORMULA VI wherein $R_1$, $R_2$, $R_3$, $R_4$ and $R_5'$ are as defined above; with a hydride reducing agent such as lithium aluminum hydride, diborane or sodium bis(2-methoxyethoxy)aluminum hydride, in an inert solvent such as tetrahydrofuran, ethyl ether or toluene, in the temperature range from about 0° C. to about 120° C. Compounds represented by Formula VI may be prepared by [2+2]photocycloaddition of an enol ether represented by Formula VII:

$CH_2=CHOR_9$ 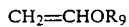 FORMULA VII wherein $R_9$ is $C_1-C_3$ alkyl, to a maleimide represented by Formula VIII:

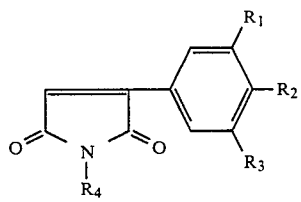

FORMULA VIII wherein $R_1$, $R_2$, $R_3$ and $R_4$ are as described above, using ultraviolet light, in the absence of a cosolvent, or in an inert solvent such as dichloromethane. Maleimides of Formula VIII may be prepared by methods described by Izzo, J. Org. Chem., 28: 1713 (1963).

Alternatively, compounds of Formula I, wherein $R_1$, $R_2$, $R_3$ and $R_4$ are as described above, and $R_5$ is $C_1-C_3$ alkoxyl, may be prepared by the alkylation of an alcohol represented by Formula IX:

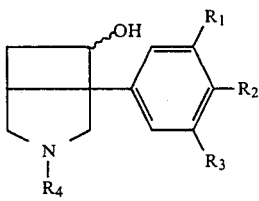

FORMULA IX wherein $R_1$, $R_2$, $R_3$ and $R_4$ are as described above, using a base such as an alkali metal, e.g., potassium, or a metal hydride such as sodium hydride, or lithium hydride, in an inert solvent such as diethyl ether, or tetrahydrofuran, to form an alkoxide, followed by reaction with an alkylating agent represented by Formula X:

$R_9-X$  FORMULA X wherein $R_9$ is as described above, and X is a suitable leaving group, such as a bromo, iodo, methanesulfonyloxy, or a p-toluenesulfonyloxy group. Alcohols represented by Formula IX may be prepared from ketones represented by Formula III by reduction with a hydride such as sodium borohydride in an alcohol, such as methanol, or lithium aluminum hydride in an inert solvent, such as tetrahydrofuran, or by the Meerwein-Ponndorf-Verley procedure, using aluminum isopropoxide in isopropyl alcohol.

Processes for synthesis of these and similar compounds, are described in U.S. Pat. No. 4,431,661 filed Aug. 20, 1981, under Ser. No. 294,548. The disclosure of such patent is hereby incorporated by reference.

The following are presented as examples illustrating the present invention, without limiting the scope hereof.

EXAMPLE 1

5-(m-Methoxyphenyl)-3-methyl-spiro[3-azabicyclo[3.2.0]heptane-6,2'-[1,3]-dithiolane] and fumarate salt A mixture of about 3.07 g of 5-(m-methoxyphenyl)-3-methyl-3-azabicyclo[3.2.0]heptane-6-one, about 4 ml of ethanedithiol and about 4 ml of freshly distilled boron trifluoride etherate in about 40 ml of acetic acid was stirred at room temperature for approximately 3 days. The volatiles were removed at reduced pressure and the residue partitioned with ether and about 10% hydrochloric acid. The aqueous phase was made basic with about 10N sodium hydroxide and filtered to give about 3.36 g of a yellow solid, m.p. 113°-117° C. The analytical sample was recrystallized from isopropyl ether/chloroform, m.p. 116°-118° C.

An approximately 218 mg portion of the solid was taken up in about 2 ml of acetone and added to a solution of about 90 mg of fumaric acid in about 10 ml of boiling acetone. Cooling to about 5° C. and filtration gave about 0.11 g of a white solid, m.p. 149°-151° C. Dilution with ether gave an additional approximately 0.15 g, m.p. 149°–150° C., and a third crop of about 0.02 g, m.p. 145°–149° C. was also obtained.

EXAMPLE 2

1-(m-Methoxyphenyl)-3-methyl-3-azabicyclo[3.2.0]heptane, and fumarate salt monohydrate Approximately 20 ml of Raney nickel was washed under a stream of distilled water until the washings were neutral. The catalyst was then washed with approximately 5 portions of ethanol and added to about 2.75 g of 5-(m-methoxyphenyl)-3-methyl-spiro[3-azabicyclo[3.2.0]heptane-6,2'-[1,3]-dithiolane]. The mixture was diluted with ethanol to about 150 ml and heated at reflux for about 1½ hours. The warm reaction mixture was filtered and evaporated to give about 1.82 g of a colorless liquid. The reference sample was prepared by Kugelrohr distillation at about 105° C./30μ. The free base was added to a solution of about 0.95 g of fumaric acid in about 50 ml of boiling acetone. The oil, which separated upon cooling to about 5° C. was decanted and allowed to stand in the air whereupon it solidified to give the fumarate salt as a white gummy solid, m.p. 116°–127° C. Elemental analysis revealed this salt to be a fumarate hydrate.

EXAMPLE 3

5-(p-Methylphenyl)-3-methyl-spiro[3-azabicyclo[3.2.0]heptane-6,2'-[1,3]-dithiolane]

A stirred mixture of about 4.1 g of 6,6-dimethoxy-5-(p-methyl-phenyl)-3-azabicyclo[3.2.0]heptane and about 50 ml of approximately 10% hydrochloric acid was heated under reflux for about 30 minutes. The solution was made basic with 5N sodium hydroxide and then was extracted with dichloromethane. The extract was dried over sodium sulfate, filtered, and evaporated under reduced pressure to give about 2.8 g of 5-(p-methylphenyl)-3-azabicyclo[3.2.0]heptane-6-one, b.p. 125°–130° C. (0.2 mm), as a yellow liquid. The fumarate salt had m.p. 130°–133° C. A mixture of about 3.8 g of the ketone, about 5 ml of 1,2-ethanedithiol and about 5 ml of freshly distilled boron trifluoride etherate in about 40 ml of acetic acid was stirred at room temperature for approximately 4 days, and then was evaporated under reduced pressure to give a tarry residue. This residue was slurried with ether and about 10% hydrochloric acid, and then the aqueous phase was made basic with approximately 5N sodium hydroxide and extracted with dichloromethane. The extract was dried over sodium sulfate and evaporated to give about 4.1 g of a solid. Recrystallization from acetonitrile gave 5-(p-methylphenyl)-3-methyl-spiro[3-azabicyclo[3.2.0]heptane-6,2'-[1,3]-dithiolane] as a tan solid, m.p. 81°–86° C.

Following essentially the procedure of Example 3 the products of Examples 4–7, found in Table I, may be prepared by hydrolyzing the indicated ketals (described in U.S. Pat. No. 4,431,661, filed Aug. 20, 1981 under Ser. No. 294,548 and incorporated by reference herein) to the corresponding ketones and then conversion to the corresponding thioketals.

TABLE I

| Example | Ketal | Ketone | Thioketal |
|---|---|---|---|
| 4 | 6,6-dimethoxy-5-(p-chlorophenyl)-3-methyl-3-azabicyclo[3.2.0]-heptane, fumarate | 5-(p-chlorophenyl)-3-methyl-3-azabicyclo-[3.2.0]heptan-6-one | 5-(p-chlorophenyl)-3-methylspiro-3-azabicyclo-[3.2.0]heptane-6,2'-[1,3]-dithiolane |
| 5 | 6,6-dimethoxy-3-methyl-5-(3',4',5'-trimethoxyphenyl)-3-azabicyclo[3.2.0]heptane | 3-methyl-5-(3',4',5'-trimethoxyphenyl)-3-azabicyclo[3.2.0]heptan-6-one | 3-methyl-5-(3',4',5'-trimethoxyphenyl)-3-azabicyclo[3.2.0]heptane-6,2'-[1,3]-dithiolane |
| 6 | 6,6-dimethoxy-3-methyl-5-phenyl-3-azabicyclo-[3.2.0]heptane | 3-methyl-5-phenyl-3-azabicyclo[3.2.0]heptan-6-one | 3-methyl-5-phenyl-3-azabicyclo[3.2.0]heptane-6,2'-[1,3]-dithiolane |
| 7 | 6,6-dimethoxy-5-(m-methoxyphenyl)-3-azabicyclo[3.2.0]heptane, fumarate | 5-m-methoxyphenyl)-3-azabicyclo[3.2.0]heptan-6-one | 5-(m-methoxyphenyl)-3-azabicyclo[3.2.0]heptane-6,2'-[1,3]dithiolane |

EXAMPLE 8

1-(p-Methylphenyl)-3-methyl-3-azabicyclo[3.2.0]heptane, and fumarate salt

Approximately 20 ml of Raney nickel was washed with distilled water to neutrality, and then with ethanol. The catalyst was then added to a solution of about 3.4 g of 5-(p-methylphenyl)-3-methyl-spiro[3-azabicyclo[3.2.0]heptane-6,2'-[1,3]-dithiolane] in about 150 ml of ethanol, and this was refluxed for approximately 2 hours. Filtration and then evaporation of the filtrate gave about 1.5 g of 1-(p-methylphenyl)-3-methyl-3-azabicyclo[3.2.0]heptane as a colorless liquid, b.p. 125° C. (0.1 mm). This was combined with fumaric acid in acetone to give the fumarate as a straw-colored glass.

Following essentially the procedure of Example 8, the products of Examples 9–12, found in Table II, may be prepared by reduction of the indicated thioketals.

TABLE II

| Example | Thioketal | Product |
|---|---|---|
| 9 | 5-(p-chlorophenyl)-3-methyl-spiro-3-azabicyclo[3 · 2 · 0]heptane-6,2'-[1,3]-dithiolane | 1-(p-chlorophenyl)-3-methyl-3-azabicyclo-[3 · 2 · 0]heptane |
| 10 | 3-methyl-5-(3',4',5'-trimethoxyphenyl)-3-azabicyclo[3 · 2 · 0]heptane-6,2'-[1,3]-dithiolane | 3-methyl-1-(3',4',5'-trimethoxyphenyl)-3-azabicyclo[3 · 2 · 0]heptane |
| 11 | 3-methyl-5-phenyl-3-azabicyclo[3 · 2 · 0]heptane-6,2'-[1,3]-dithiolane | 3-methyl-1-phenyl-3-azabicyclo[3 · 2 · 0]heptane |
| 12 | 5-(m-methoxyphenyl)-3-azabicyclo[3 · 2 · 0]heptane-6,2'-[1,3]-dithiolane | 1-(m-methoxyphenyl)-3-azabicyclo[3 · 2 · 0]heptane |

EXAMPLE 13

1-(m-Methoxyphenyl)-3-propyl-3-azabicyclo[3.2.0]heptane hydrochloride

A mixture of 1-(m-methoxyphenyl)-3-azabicyclo[3.2.0]heptane, n-propyl bromide and sodium carbonate in toluene is refluxed for approximately 6 hours.

The mixture is washed with water, and the organic phase is dried over sodium sulfate and then evaporated. The residual oil is dissolved in ether, and then hydrogen chloride gas is passed into this solution. The crystalline product is recrystallized from acetonitrile to give 1-(m-methoxyphenyl)-3-propyl-3-azabicyclo[3.2.0]heptane hydrochloride.

EXAMPLE 14

1-(3',4'-Dichlorophenyl)-3-methyl-3-azabicyclo[3.2.0]heptane

A solution of 4,4-dimethoxy N-methyl-1-(3',4'-dichlorophenyl)-1,2-cyclobutanedicarboximide, (m.p. 158°–161° C.) (disclosed and described in U.S. Pat. No. 4,431,661 filed Aug. 20, 1981 under Ser. No. 294,548, and incorporated herein by reference) in tetrahydrofuran is added to excess about 1N borane-tetrahydrofuran at about 0° C., and this solution is stirred and allowed to warm to room temperature (about 15°–25° C.) over approximately 3 hours. Excess about 1N hydrochloric acid is added and the solution is warmed on a steam bath for approximately 15 minutes. The tetrahydrofuran is removed under reduced pressure, the aqueous solution is made basic with sodium hydroxide, and this is extracted with ether. The extract is dried over sodium sulfate and evaporated to give 3-methyl-5-(3',4'-dichlorophenyl)-3-azabicyclo[3.2.0]heptan-6-one. This ketone is reacted with 1,2-ethanedithiol by the procedure of Example 1 to give 5-(3',4'-dichlorophenyl)-3-methyl-spiro[3-azabicyclo[3.2.0]heptane-6,2'-[1,3]-dithiolane. This is reacted with Raney nickel by the procedure of Example 2 to give 1-(3',4'-dichlorophenyl)-3-methyl-3-azabicyclo[3.2.0]heptane.

EXAMPLE 15

7β-Ethoxy-1β-(m-methoxyphenyl)-3-methyl-3-azabicyclo[3.2.0]heptane

To about 50 ml of ethyl vinyl ether was added a solution of about 2.55 g of 2-(m-methoxyphenyl)-N-methyl maleimide in about 50 ml of dichloromethane over approximately 2 hours, while the stirred solution was being irradiated with a 400 watt, high-pressure, ultraviolet lamp. Evaporation under reduced pressure gave approximately 2.09 g of brown oil, and this was chromatographed using high performance liquid chromatography. The first fraction using about 6% ether in dichloromethane was 4β-ethoxy-1β-(m-methoxyphenyl)-N-methyl-1,2-cyclobutanedicarboxamide. A mixture of about 0.38 g of this imide and about 5 ml of sodium bis(2-methoxyethoxy)aluminum hydride (about 70% in toluene) in about 50 ml of toluene was stirred for approximately 18 hours and then was heated at reflux for about 3 hours. The solution was cooled, decomposed with dilute sodium hydroxide, and the organic phase was dried over sodium sulfate. Evaporation gave about 0.30 g 7β-ethoxy-1β-(m-methoxyphenyl)-3-methyl)-3-azabicyclo[3.2.0]heptane, b.p. 130° C. (0.1 mm).

EXAMPLE 16

7α-Ethoxy-1β-(m-methoxyphenyl)-3-methyl-3-azabicyclo[3.2.0]heptane

The second chromatographic fraction of Example 15 was distilled to give 4α-ethoxy-1β-m-methoxyphenyl-N-methyl-1,2-cyclobutanedicarboximide, b.p. 160° C. (0.07 mm).

A mixture of about 0.75 g of the above imide and about 10 ml of sodium bis(2-methoxyethoxy)aluminumhydride (about 70% in toluene) in 20 ml of toluene was heated to about 110° C. at reflux for approximately 4 hours. The solution was cooled to about 10° C., about 10 ml of about 10N sodium hydroxide was added, the organic layer was dried over sodium sulfate and evaporated. The residual liquid was distilled to give about 0.67 g 7α-ethoxy-1β-(m-methoxyphenyl)-3-methyl-3-azabicyclo[3.2.0]heptane as a colorless liquid, b.p. 105° C. (0.05 mm). The fumarate salt had a m.p. 136°–138° C.

What is claimed is:

1. Compounds, including optically active isomers and racemic mixtures, represented by the formula:

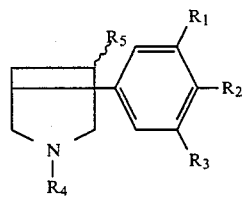

wherein $R_1$, $R_2$ and $R_3$ are each selected from the group consisting of hydrogen, hydroxy, chloro, fluoro, bromo, $C_1$–$C_3$ alkyl, $C_1$–$C_3$ alkoxy and trifluoromethyl and any two or more of $R_1$, $R_2$ and $R_3$ may be the same; $R_4$ is selected from the group consisting of hydrogen and $C_1$–$C_3$ alkyl; and $R_5$ is hydrogen or alkoxy; and the non-toxic, pharmacologically acceptable acid-addition salts thereof.

2. The compound according to claim 1 which is 1-(m-methoxyphenyl)-3-methyl-3-azabicyclo[3.2.0]heptane.

3. The compound according to claim 1 which is 1-(m-methoxyphenyl)-3-methyl-3-azabicyclo[3.2.0]heptane, fumarate.

4. The compound according to claim 1 which is 1-(p-methylphenyl)-3-methyl-3-azabicyclo[3.2.0]heptane.

5. The compound according to claim 1 which is 1-(p-methylphenyl)-3-methyl-3-azabicyclo[3.2.0]heptane, fumarate.

6. The compound according to claim 1 which is 7β-ethoxy-1β-(m-methoxyphenyl)-3-methyl-3-azabicyclo[3.2.0]heptane.

7. The compound according to claim 1 which is 7α-ethoxy-1β-(m-methoxyphenyl)-3-methyl-3-azabicyclo[3.2.0]heptane.

8. The compound according to claim 1 which is 7α-ethoxy-1β-(m-methoxyphenyl)-3-methyl-3-azabicyclo[3.2.0]heptane, fumarate.

9. A method of treating depression in a warm-blooded animal, which method comprises administering to said animal a therapeutically effective amount of a compound, including optically active isomers and racemic mixtures, represented by the formula:

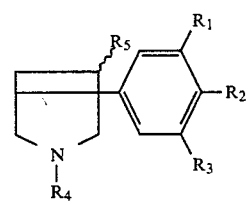

wherein $R_1$, $R_2$ and $R_3$ are each selected from the group consisting of hydrogen, hydroxy, chloro, fluoro, bromo, $C_1$–$C_3$ alkyl, $C_1$–$C_3$ alkoxy, and trifluoromethyl, and any two or more of $R_1$, $R_2$ and $R_3$ may be the same; $R_4$ is selected from the group consisting of hydrogen and $C_1$–$C_3$ alkyl; and $R_5$ can be either hydrogen or alkoxyl; and the nontoxic pharmacologically acceptable acid-addition salts thereof.

10. The method according to claim 9, wherein the compound is 1-(m-methoxyphenyl)-3-methyl-3-azabicyclo[3.2.0]heptane.

11. The method according to claim 9, wherein the compound is 1-(m-methoxyphenyl)-3-methyl-3-azabicyclo[3.2.0]heptane, fumarate.

12. The method according to claim 9, wherein the compound is 1-(p-methylphenyl)-3-methyl-3-azabicyclo[3.2.0]heptane.

13. The method according to claim 9, wherein the compound is 1-(p-methylphenyl)-3-methyl-3-azabicyclo[3.2.0]heptane, fumarate.

14. The method according to claim 9, wherein the compound is 7β-ethoxy-1β-(m-methoxyphenyl)-3-methyl-3-azabicyclo[3.2.0]heptane.

15. The method according to claim 9, wherein the compound is 7α-ethoxy-1β-(m-methoxyphenyl)-3-methyl-3-azabicyclo[3.2.0]heptane.

16. The method according to claim 9, wherein the compound is 7α-ethoxy-1β-(m-methoxyphenyl)-3-methyl-3-azabicyclo[3.2.0]heptane, fumarate.

* * * * *